(12) United States Patent
Lee

(10) Patent No.: US 7,977,473 B1
(45) Date of Patent: Jul. 12, 2011

(54) USE OF NON-CRYSTALLINE CELLULOSE AS A MEDICINE TABLET MEDIUM

(75) Inventor: Yoon Y. Lee, Auburn, AL (US)

(73) Assignee: Auburn University, Auburn, IL (US)

( * ) Notice: Subject to any disclaimer, the term of this patent is extended or adjusted under 35 U.S.C. 154(b) by 450 days.

(21) Appl. No.: 12/214,661

(22) Filed: Jun. 20, 2008

Related U.S. Application Data

(63) Continuation-in-part of application No. 11/142,936, filed on Jun. 2, 2005.

(60) Provisional application No. 60/576,103, filed on Jun. 2, 2004, provisional application No. 60/936,749, filed on Jun. 22, 2007.

(51) Int. Cl.
*C08B 16/00* (2006.01)
*C08B 1/00* (2006.01)
*C08B 9/00* (2006.01)

(52) U.S. Cl. .................................. 536/56; 536/57

(58) Field of Classification Search .................. None
See application file for complete search history.

(56) References Cited

U.S. PATENT DOCUMENTS

| | | | |
|---|---|---|---|
| 2,758,112 A | 8/1956 | Waning et al. | 260/212 |
| 3,397,198 A | 8/1968 | Greidinger et al. | 260/212 |
| 4,058,411 A | 11/1977 | Bellamy et al. | 127/37 |
| 4,239,906 A | 12/1980 | Antrim et al. | |
| 4,266,981 A | 5/1981 | Tsao et al. | 127/37 |
| 4,357,467 A | 11/1982 | Sachetto et al. | 536/56 |
| 4,752,579 A | 6/1988 | Arena et al. | |
| 5,417,984 A | 5/1995 | Banker et al. | 424/488 |
| 5,597,714 A | 1/1997 | Farone et al. | 435/100 |
| 5,674,507 A | 10/1997 | Banker et al. | 424/401 |
| 6,627,749 B1 | 9/2003 | Kumar | 536/56 |
| 2004/0217063 A1 | 11/2004 | Zhang et al. | 210/723 |
| 2008/0132560 A1* | 6/2008 | Chow et al. | 514/415 |

OTHER PUBLICATIONS

Kunshreshtha et al., "Paracrystalline Lattice Disorder in Cellulose. Reappraisal of the Application of the Two-Phase Hypothesis to the Analysis of Powder X-Ray Diffractograms of Native and Hydrolyzed Cellulosic Materials." Journal of Polymer Science (1973) vol. 11 pp. 487-497.*

Mihranyan et al., "Moisture sorption by cellulose powders of varying crystallinity" International Journal of Pharmaceutics (2004) vol. 269 pp. 433-442.*

"Merriam-Webster's Collegiate Dictionary, Tenth Edition", 1998, p. 1107, Merriam-Webster, Inc.

H. Boerstoel et al., "Liquid crystalline solutions of cellulose in phosphoric acid", 2001, pp. 7371-7379, vol. 42, Elsevier Science Ltd., www.elsevier.n/locate/polymer.

F. Camacho et al., "Microcrystalline-Cellulose Hydrolysis with Concentrated Sulphuric Acid",1996,pp. 350-356, J. Chem. Tech. Biotechnol., vol. 67.

Juinn-Chin Hsu et al., "Preparation and Utilization of Cellulose Substrates Regenerated after Treatment with Hydrochloric Acid", 1991, pp. 1444-1447, vol. 39, J. Agric. Food Chem., American Chemical Society.

Stalbrand et al., "Analysis of Molecular Size Distributions of Cellulose Molecules during Hydrolysis of Cellulose by Recombinant Cellulomonas fimi B-1,4-Glucanasses", Jul. 1998, pp. 2374-2379, vol. 64, No. 7, Applied and Environmental Microbiology.

Peri et al., "Kinetic Investigation of Cellulase Enzyme Using Non-Crystalline Cellulose and Celllo-Oligosaccharides", Poster Presentation 1B-60, 27$^{th}$ Symposium on Biotechnology for Fuels and Chemicals, Dept. of Energy, Denver, Co, May 1, 2005.

* cited by examiner

*Primary Examiner* — Eric S Olson
(74) *Attorney, Agent, or Firm* — Haverstock & Owens LLP

(57) ABSTRACT

A non crystalline or low crystallinity cellulose is able to be formed into a medicine tablet medium. A method of making a tablet of non crystalline or low crystallinity cellulose comprises providing cellulosic material, adding an effective acid in an amount effective to at least wet the cellulosic material, mixing the cellulosic material and acid under conditions effective to form an essentially uniformly wet condition, letting the mixture sit at ambient conditions for a period of time sufficient to form a viscous fluid, adding water or other diluent in an amount sufficient to lower the acid concentration and to form a slurry, dewatering the slurry, removing any residual acid from the dewatered slurry and forming the tablet.

17 Claims, 12 Drawing Sheets

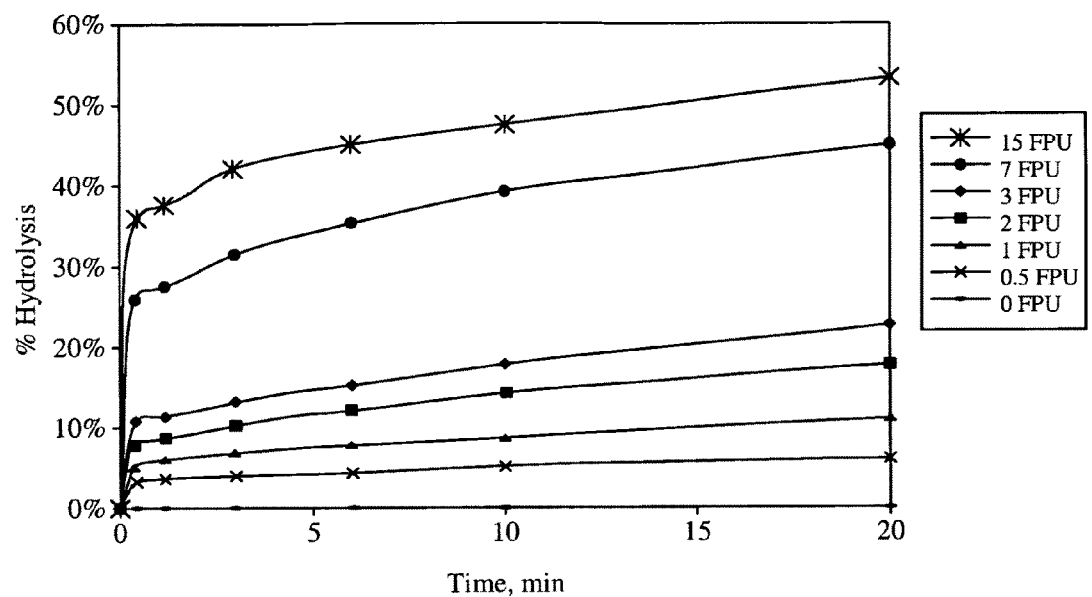
Fig. 3 (con't.)

USE OF NON-CRYSTALLINE CELLULOSE AS A MEDICINE TABLET MEDIUM

CROSS-REFERENCE TO RELATED APPLICATIONS

This application is a continuation-in-part of co-pending U.S. patent application Ser. No. 11/142,936, filed on Jun. 2, 2005 and entitled "Non-crystalline cellulose and production thereof" which claims the benefit of U.S. Provisional Patent Application Ser. No. 60/576,103, filed Jun. 2, 2004, both of which are hereby incorporated herein by reference in their entireties for all purposes.

This application also claims the benefit of U.S. Provisional Patent Application Ser. No. 60/936,749, filed Jun. 22, 2007 and entitled "USE OF NON-CRYSTALLINE CELLULOSE AS A MEDICINE TABLET MEDIUM" which is hereby incorporated herein by reference in its entirety for all purposes.

GOVERNMENT INTEREST

This invention was made with government support under IFAFS Contract No. 5-36275 awarded by the United States Department of Agriculture. The government may have certain rights in the invention.

FIELD OF THE INVENTION

The present invention relates generally to a treated cellulose which is a non-crystalline or low crystallinity cellulose and a method for making it. The invention also relates to uses for the non-crystalline or low crystallinity cellulose.

BACKGROUND OF THE INVENTION

Cellulose is the most abundant structural biopolymer. All forms of plant life contain cellulose. Because of its nearly ubiquitous distribution in nature and human kind's long exposure to cellulose, cellulose and its derivatives are generally recognized as the safest and most acceptable polymer class for use in food and pharmaceutical products.

Cellulose is a solid natural carbohydrate polymer (polysaccharide) composed of anhydroglucose units (β-D glucopyranose rings) joined by an oxygen linkage (β-1,4-glycosidic linkage) and has the empirical formula $(C_6H_{10}O_5)_n$. Cellulose is insoluble in water and organic solvents. It will swell in sodium hydroxide solutions and is soluble in Schweitzer's reagent. Cellulose exists in three forms—α, β, and γ. α-cellulose has the highest degree of polymerization and is the chief constituent of paper pulp. It is insoluble in strong sodium hydroxide solution. The β and γ forms have much lower DP and are known as hemicellulose. Cellulose can be decomposed to glucose by the enzyme cellulase or by hydrolysis.

Cellulose is a complex composite material which structurally comprises three hierarchical levels: (i) The molecular level of the single molecule; (ii) the supermolecular level concerning the packing and aggregation of the molecules in crystals called microfibrils; and (iii) the morphological level, i.e., the arrangement of microfibrils and interstitial voids in relation to the cell wall. On the molecular level, the linear chains of glucose units form whisker-like crystals which are assembled into the superstructure. The structural organization at all levels influences the macroscopic properties of the material and is equally of importance for the chemical reactions taking place during processing.

The "classical" model of cellulose, however, is two-phase, assuming a composite arrangement of distinct crystalline and extended amorphous regions (H. Krssig, Cellulose: Structure, Accessibility and Reactivity; Polymer Monographs 11, Gordon and Breach Science Publ.: Yverdon 1993). Concepts like crystallinity and amorphicity have been used to describe homogeneous states of matter such as in the "classical" cellulose model. (These concepts can be, however, rather ill-defined when it comes to treat dense composite materials like cellulose given that intermolecular correlations do not build up or die off abruptly at some fictitious interfaces.) Depending on the degree of order of arrangement and hydrogen bonding between cellulose chains, the crystallinity of cellulose may range from 50% to 90%. The crystallinity of native cellulose is about 70% (P. H. Hermans and A. Weidinger, J. Poly. Sci., IV, 135 (1949)).

Chemical reagents react with or penetrate the amorphous regions much more readily than the crystalline regions. Depolymerization of cellulose by acid or enzyme hydrolysis is limited by the degree of crystallization. The amorphous and crystalline regions in cellulose fibers behave differently in most chemical reactions such as dyeing, swelling, and oxidation. Therefore, it is often of interest to determine the crystalline fraction of cellulose or process cellulose to alter the structure to make it more amorphous.

The reactions of cellulose with mineral acids to prepare non-fibrous, low molecular weight (i.e., low degree of polymerization) cellulose products suitable for use in food, cosmetics, pharmaceutical, and like products, have been studied. The reactivity of cellulose towards acids depends on the crystallinity of the cellulose source, acid concentration, and the reaction temperature and duration.

There are modified celluloses and "amorphous" celluloses. Microcrystalline cellulose (MCC) is one form of modified cellulose. The "amorphous" cellulose known to this point is cellulose chemically bound to another organic substance. An example is carboxymethylcellulose (CMC). Phosphoric acid swollen cellulose (PASC) is also known. PASC is produced by swelling MCC in concentrated phosphoric acid; though often described as amorphous, it is probably a low-crystallinity form of cellulose 11. Atalla, R. H.1993. The structures of native celluloses, p. 25-39. In P. Suominen, and T. Reinikainen (ed.), *Trichoderma reesei* cellulases and other hydrolases. Foundation for Biotechnical and Industrial Fermentation, Helsinki, Finland.

SUMMARY OF THE INVENTION

The present invention includes a treated cellulose which is a non-crystalline or low crystallinity cellulose (hereafter referred to as "NCC") and a method of making it.

In one aspect, the present invention includes a treated cellulose which is a non-crystalline or low crystallinity cellulose ("NCC") and compositions comprising the NCC. The NCC can be identified by particular properties and/or its relative differences to cellulose. A polymer or co-polymer can comprise a NCC of the invention.

In another aspect, the invention includes a treated cellulose which is a non-crystalline or low crystallinity cellulose produced by a method comprising providing cellulosic material, adding an effective acid in an amount effective to at least wet the cellulosic material, mixing under conditions effective to form an essentially uniformly wet condition, letting the mixture sit at ambient conditions for a period of time sufficient to form a viscous fluid, adding water or other diluent in amount sufficient to lower the acid concentration and to form a slurry, dewatering the slurry, and removing any residual acid from the dewatered slurry to form the NCC. A preferred acid is a strong acid such as concentrated sulfuric acid. The dewatered slurry can be neutralized. The NCC can also be dried and sized.

In still another aspect, the invention includes an application of the NCC, for example, fiber, fabric, foam, molded product, absorbent, paper, hydrogel, food additive, pharmaceutical additive, growth medium, reagent for testing enzyme activity, and the like.

In a further aspect, the invention includes further processing the NCC for the purposes of producing chemicals or fuels via fermentation or other chemical processes.

A non crystalline or low crystallinity cellulose is able to be formed into a medicine tablet medium. A method of making a tablet of non crystalline or low crystallinity cellulose comprises providing cellulosic material, adding an effective acid in an amount effective to at least wet the cellulosic material, mixing the cellulosic material and acid under conditions effective to form an essentially uniformly wet condition, letting the mixture sit at ambient conditions for a period of time sufficient to form a viscous fluid, adding water or other diluent in an amount sufficient to lower the acid concentration and to form a slurry, dewatering the slurry, removing any residual acid from the dewatered slurry and forming the tablet.

In another aspect, a tablet comprises a treated cellulose having the following properties: melting point by differential scanning calorimeter (DSC) of about 260° C., bulk density of about 0.2 g/cm$^3$ in freeze-dried powder form, bulk density of about 0.8 g/cm$^3$ in air-dried and ground powder form, enzymatic hydrolysis profile using 1 filter paper unit (FPU) cellulase/1 cellobiase unit (CBU) β-glucosidase demonstrating at least about 30% hydrolysis at 15 FPU, at least about 20% hydrolysis at 7 FPU, and at least about 5% hydrolysis at 1 FPU, water absorption capacity of at least about 6 to about 8 times its weight in water and morphology without a rigid crystalline structure but rather a sponge-like structure. The cellulase is Spezyme® CP and the β-glucosidase is Novozym® 188. The treated cellulose is highly hygroscopic. No foreign substances are added to the tablet. The tablet further has the property of rapid dispersion in water. The tablet further has the property of an open macro structure. The tablet further has the property of a steady and even medicine release pattern.

In another aspect, a tablet comprises a treated cellulose having the following properties: lower melting point by DSC than α-cellulose, bulk density in the freeze dried powder form essentially the same as α-cellulose, bulk density in the air-dried and ground powder form higher than that of α-cellulose, greater enzymatic hydrolysis using 1 FPU cellulase/1 CBU β-glucosidase than α-cellulose at the same concentration of enzyme, FTIR spectrum different than that of α-cellulose, including a lower absorbance near 1429 cm-1 and a higher absorbance near 1162 cm-1, more hygroscopic than α-cellulose, water absorption capacity higher than that of α-cellulose, X ray diffraction pattern showing a lower major peak and additional minor peaks as compared to α-cellulose or microcrystalline cellulose, morphology that is more homogeneous and has higher connectivity relative to α-cellulose morphology, higher surface area per unit mass than α-cellulose, different porosity than α-cellulose and higher viscosity than α-cellulose when added to water at similar concentrations. The cellulase is Spezyme® CP and the β-glucosidase is Novozym® 188. The tablet of claim 8 wherein the melting point is about 80° C. lower than α-cellulose, bulk density in the air-dried and ground powder is about 4 times higher than that of α-cellulose, about 2 orders of magnitude greater enzymatic hydrolysis than α-cellulose at the same concentration of enzyme, FTIR spectrum different than that of α-cellulose, including an absorbance about 10-15% lower at 1429 cm$^{-1}$ and an absorbance about 30-60% higher near 1162 cm$^{-1}$, water absorption capacity about 5 to about 25 times higher than that of α-cellulose and X ray diffraction pattern having a lower peak at 2θ=22° and additional minor peaks at higher values of 2θ as compared to α-cellulose or microcrystalline cellulose. In another aspect, no foreign substances are added to the tablet. The tablet further has the property of rapid dispersion in water. The tablet further has the property of an open macro structure. The tablet further has the property of a steady and even medicine release pattern.

In another aspect, a method of generating a tablet of a treated cellulose comprises providing cellulosic material, adding an effective acid in an amount effective to at least wet the cellulosic material, mixing the cellulosic material and acid under conditions effective to form an essentially uniformly wet condition, letting the mixture sit at ambient conditions for a period of time sufficient to form a viscous fluid, adding water or other diluent in an amount sufficient to lower the acid concentration to quench a reaction between the cellulosic material and acid and to form a slurry, dewatering the slurry, removing any residual acid from the dewatered slurry to form the treated non-crystalline or low crystallinity cellulose and forming the cellulose into a tablet. Forming the cellulose into the tablet is by compression. A range of 8-30 kiloponds of hardness is applied when forming the tablet. Forming the cellulose into the tablet is by using a mold. No foreign substances are added to the tablet.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 1a) and 1b) are micrographs of α-cellulose and freeze-dried treated α-cellulose at ×200 magnification, respectively. FIGS. 1c) and 1d) are micrographs of α-cellulose and freeze-dried treated α-cellulose at ×1000 magnification, respectively. FIGS. 1e) and 1f) are micrographs of α-cellulose and freeze-dried treated α-cellulose at ×3000 magnification, respectively.

FIG. 3 shows the following results: a) and b) are 15 FPU results for α-cellulose (diamonds) and treated α-cellulose (NCC) (squares); c) and d) are 7 FPU results for α-cellulose (circles) and treated α-cellulose (NCC) (squares); e) and f) are 1 FPU results for α-cellulose (diamonds) and treated α-cellulose (NCC) (squares). FIG. 3 g) shows % hydrolysis of treated α-cellulose (NCC) for (from top to bottom) 15 FPU (asterisk), 7 FPU (circle), 3 FPU (diamond), 2 FPU (square), 1 FPU (triangle), 0.5 FPU (x), and 0 FPU (box) enzyme loadings.

FIG. 7A: Avicel® 1 FPU/g glucan (6 hrs.); FIG. 7B: Avicel® 1 FPU/g glucan (96 hrs.); FIG. 7C: NCC 1 FPU/g glucan (6 hrs.); FIG. 7D: NCC 1 FPU/g glucan (96 hrs.).

FIG. 9A: Enzyme loading=1 FPU/g glucan; FIG. 9B: enzyme loading=3 FPU/g glucan. Oligomers were not degraded throughout the reaction.

DETAILED DESCRIPTION OF THE PREFERRED EMBODIMENT

Figure 1:
FIG. 1 shows scanning electron microscope (SEM) pictures of untreated α-cellulose and freeze-dried treated α-cellulose ("TC", aka "NCC").
Figure 1:
Figure 1:
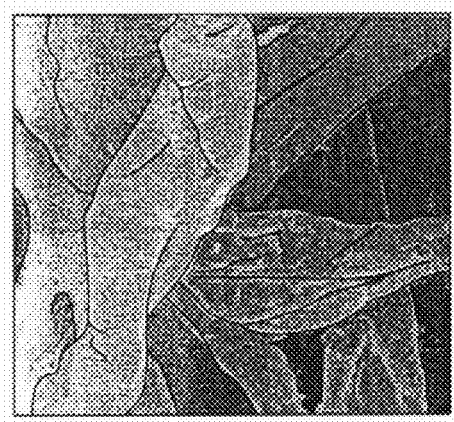
Figure 1:
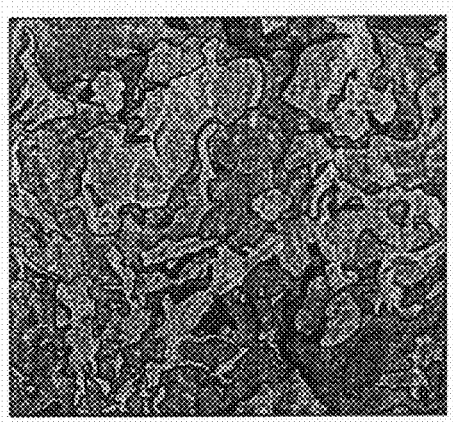
Figure 1:
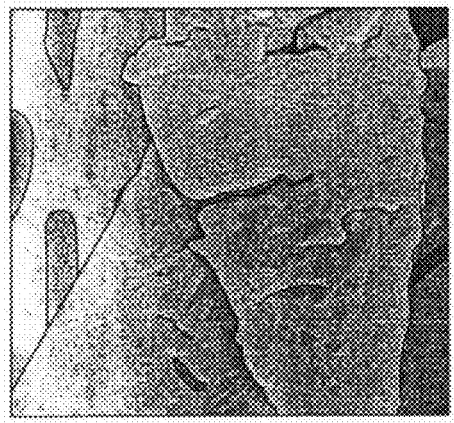
Figure 1:
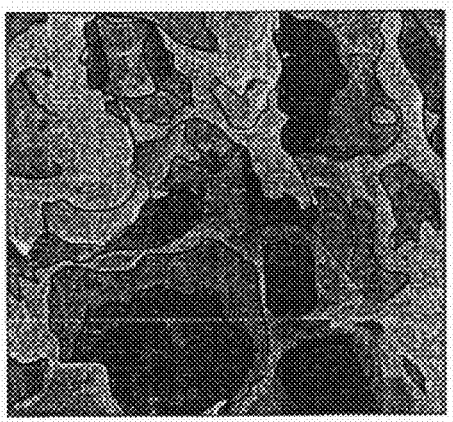

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, as they may vary, and that the terminology used herein is for the purpose of describing particular embodiments by way of example only and is not intended to be limiting of the claimed invention.

Before the present compounds, compositions, articles, devices, and/or methods are disclosed and described, it is to be understood that the terminology used herein is for the purpose of describing particular aspects only and is not intended to be limiting.

In this specification and in the claims which follow, reference will be made to a number of terms which shall be defined to have the following meanings:

It must be noted that, as used in the specification and the appended claims, the singular forms "a," "an," and "the" include plural referents unless the context clearly dictates otherwise. Thus, for example, reference to "an enzyme" includes mixtures of enzymes, reference to "a cellulosic material" includes mixtures of two or more such cellulosic materials, and the like.

"Optional" or "optionally" means that the subsequently described event or circumstance may or may not occur, and that the description includes instances where the event or circumstance occurs and instances where it does not. For example, the phrase "optionally drying" means that the drying may or may not be performed and that the description includes both undried and dried material.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Non-crystalline" or "low crystallinity" as used herein refers to the treated cellulose of the invention with reduced crystallinity relative to non-treated cellulose; as is apparent to one of ordinary skill in the art there is some residual crystallinity in the treated cellulose but it is different in amount and kind relative to untreated cellulose.

A. Compositions

The present invention includes a treated cellulose that is non-crystalline or low crystallinity cellulose ("NCC") and compositions comprising the treated cellulose ("TC" aka "NCC").

Tests (described below in the Examples) were conducted to characterize material included in the present invention. The test results, shown in the Figures, collectively prove that the crystalline cellulose existing in the starting test material is converted into non-crystalline/low crystallinity cellulose (NCC) resulting in drastically different physical properties including morphology, surface area, porosity, crystallinity, and viscosity in wet form. These changes of physical properties bring about changes in reactivity as well, for example, a more than 100 fold increase in reactivity during the initial phase of enzymatic hydrolysis with low enzyme loadings.

FIG. 1 shows SEM pictures of untreated α-cellulose and freeze-dried treated α-cellulose (NCC, aka TC) at various magnifications. The rigid fibrous structure of α-cellulose appears to have disappeared in the example treated α-cellulose of the present invention. The new material appears more homogenous, has higher connectivity, and shows a sponge-like structure.

Figure 2:
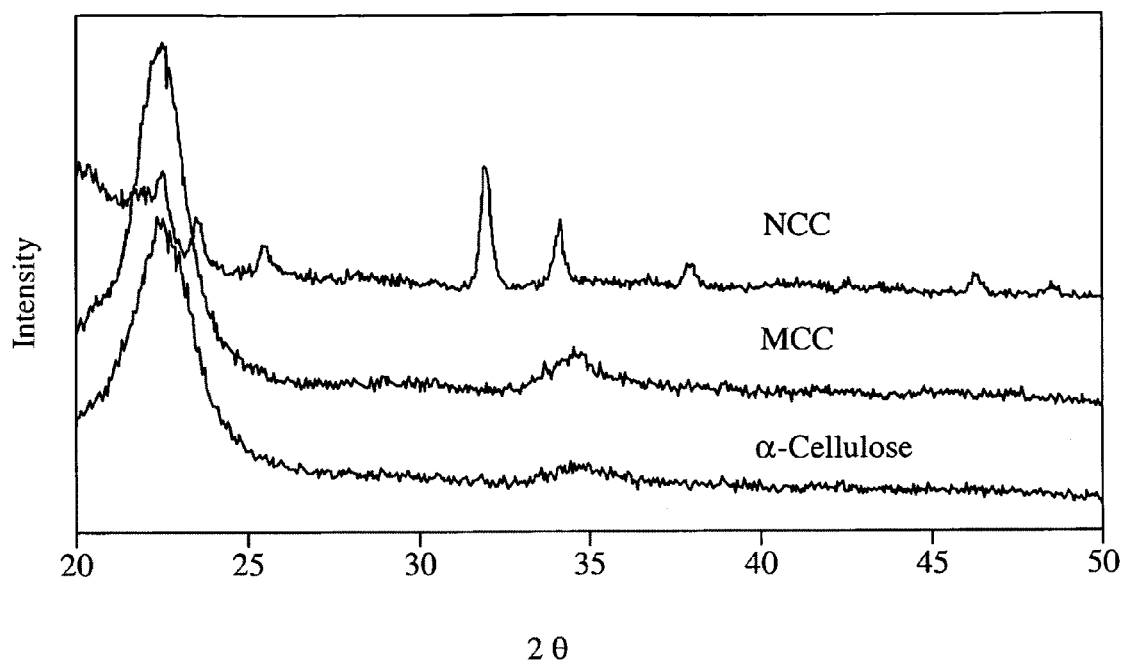
FIG. 2 shows x-ray diffraction patterns of microcrystalline cellulose (MCC), α-cellulose, and treated α-cellulose ("NCC"). There is a sharp peak at approximately 2θ=22.5° for α-cellulose. The diffraction intensity of NCC is drastically decreased. New smaller peaks of NCC indicate that partial crystallinity takes place at about 2θ=33° and about 2θ=37°.

FIG. 2 shows x-ray diffraction (XRD) patterns of microcrystalline cellulose (MCC), α-cellulose, and treated α-cellulose (NCC). At 2θ of about 22° or about 22.5°, α-cellulose and MCC both show a distinct XRD peak due to crystalline structure. In the treated α-cellulose that peak is diminished. Additional minor peaks appear in the treated α-cellulose (NCC) at higher 2θ angles (about 33° and about 37°) showing minor crystallinity of different lattice structure. The XRD patterns indicate they are distinctly different materials and that the NCC has a basically amorphous structure.

Figure 3:
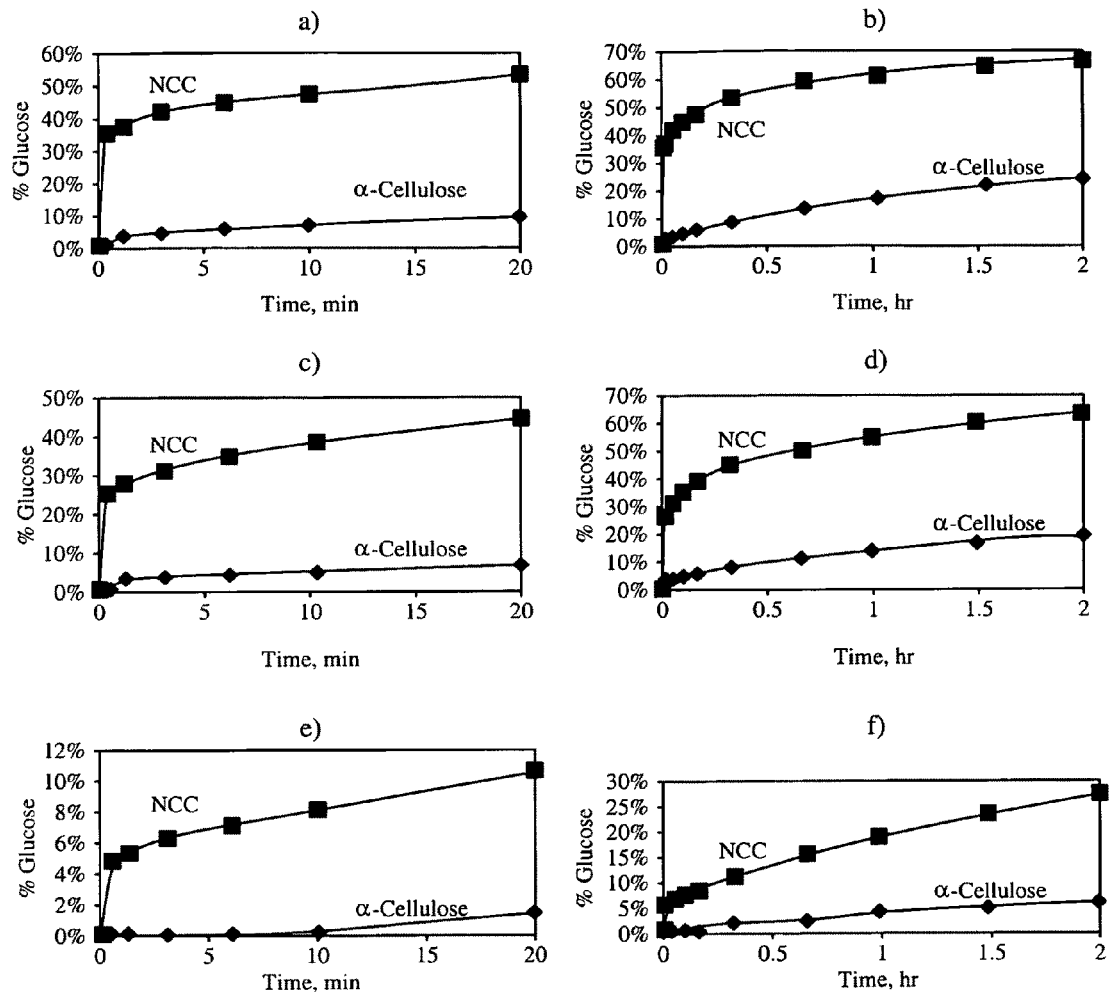
FIG. 3 shows enzymatic hydrolysis profiles with different enzyme loadings. The cellulose enzyme was Genencor Spezyme® CP supplemented with β-glucosidase (Novozym® 188) (1 filter paper unit (FPU) Spezyme®/1 cellobiase unit (CBU)).

FIG. 3 shows enzymatic hydrolysis profiles of α-cellulose (diamonds) and treated α-cellulose (squares) (NCC) with different enzyme loadings (15, 7 & 1 filter paper unit (FPU) of cellulase/g glucan). FIGS. 3 a) and b) show the 15 FPU loading; FIGS. c) and d) show the 7 FPU loading; and e) and f) show the 1 FPU loading. The cellulase enzyme used was Genencor Spezyme® CP supplemented with β-glucosidase (Novozym® 188)—1 FPU Spezyme®/1 cellobiase unit (CBU). Clearly, the enzymatic hydrolysis is greater and occurs faster in the treated cellulose (NCC) than in the untreated sample.

FIG. 3 g) shows enzymatic hydrolysis profiles of treated α-cellulose (NCC) with different enzyme loadings (15, 7, 3, 2, 1, 0.5 & 0 FPU of cellulase/g glucan). The order of the profiles from top to bottom on the graph are as expected, 15, 7, 3, 2, 1, 0.5, and 0, respectively. The cellulase enzyme was Genencor Spezymee CP supplemented with β-glucosidase (Novozym® 188)—1 FPU Spezyme®/1 CBU.

Figure 4:
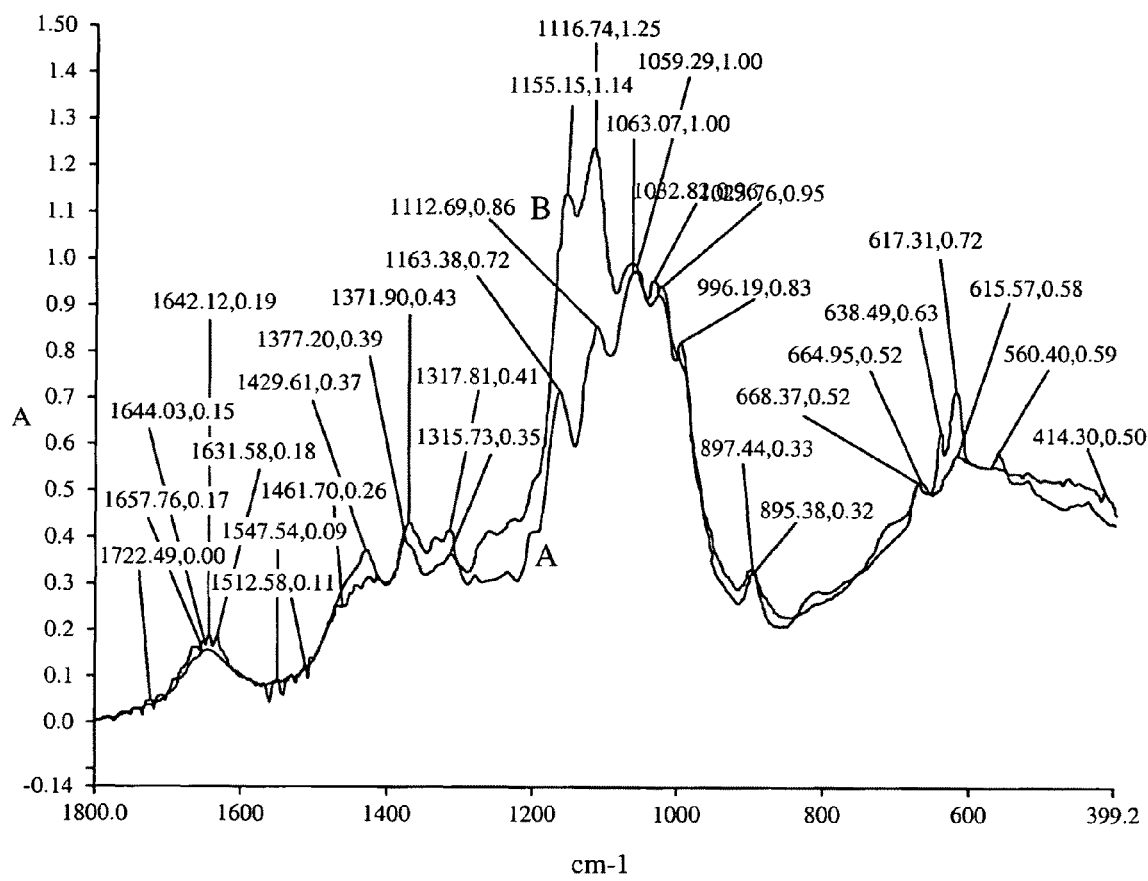
FIG. 4 shows FTIR spectra of treated (NCC) and untreated α-cellulose. Thick line A untreated α-cellulose, 1.019 (Without baseline correction); thin line B treated α-cellulose, 2.165 (Baseline correction from 1800 $cm^{-1}$ to 847.27 $cm^{-1}$). The test conditions and instrument were KBr transmission technique; spectrometer: Nicolet Avatar 360 FTIR ESP; no. of scans: 50; resolution: 4.0; and apodization: Happ-Genzel.

FIG. 4 shows Fourier Transform Infrared (FTIR) spectra (absorbance vs. wavelength (cm-1)) of treated (NCC) and untreated α-cellulose. The untreated α-cellulose is the line A-1.019 (without baseline correction). The treated α-cellulose (NCC) is the line B-2.165 (with baseline correction from 1800 $cm^{-1}$ to 847.27 $cm^{-1}$). The KBr transmission technique was used. The spectrometer was a Nicolet Avatar 360 FTIR ESP. The number of scans was 50; resolution was 4.0; and apodization was Happ-Genzel. Various references report the crystallinity of cellulose—O'Connor, et al. (1958) (O'Connor, R. T., E. F. Dupr and D. Micham, 1958, "Application of infrared absorption spectroscopy to investigations of cotton and modified cotton," Text. Res. J., 28, 382-392) A1429 $cm^{-1}$/A894 cm-1; Nelson & O'Connor (1964) (Nelson, M. L. and R. T. O'Connor, 1964, J. Appl. Polymer Sci., 8, 1311-1324; 1325-1341) A1372 cm-1/A2900 cm-1; Kemm et al. (2005) (Dieter Kemm, Brigitte Heuben, Hans-Peter Fink, and Andreas Bohn, "Cellulose: Fascination Biopolymer and Sustainable Raw Material", Angew. Chem. Int. Ed., 44, 3358-3393, 2005) A1370 $cm^{-1}$ area/A670 cm-1 area; and Hurtubise (1960) (Hurtubise, F. G. and H. Krassig, 1960, "Classification of fine structural characteristics in cellulose by infrared spectroscopy," Analytical Chem., 32, 177-181) A333 cm-1, A1163 cm-1, A900 cm-1. The main difference in the two FTIR spectra of FIG. 4 is seen in the C—O—C (glycosidic bond) asymmetric bridge oxygen stretch peak. This stretch is more prevalent in the treated cellulose (NCC), which means that the treated cellulose (NCC) has much looser (weaker) crystalline structure. The FTIR spectra of treated (NCC) and untreated α-cellulose also reveal lower absorbance values at 1429 cm-1 (O'Connor, et al., 1958) and 1372 cm-1 (Nelson & O'Connor, 1964), thus, these values suggest a decrease in crystallinity for the treated cellulose (NCC).

O'Connor, et al. defined crystallinity index for cellulose as the ratio of absorbance at 1429 $cm^{-1}$ to the absorbance at 894 $cm^{-1}$. Based on this definition, the values of crystallinity index for the two materials tested were as follows (a baseline correction was applied from 1800 $cm^{-1}$ to 847.27 $cm^{-1}$):

TABLE 1

| Crystallinity index for tested materials. | |
|---|---|
| O'Connor, et al. 1958 Crystallinity Index | $A_{1429\,cm-1}/A_{894\,cm-1}$ |
| Untreated α-cellulose | 2.506 |
| Treated α-cellulose | 2.165 |

Figure 5:
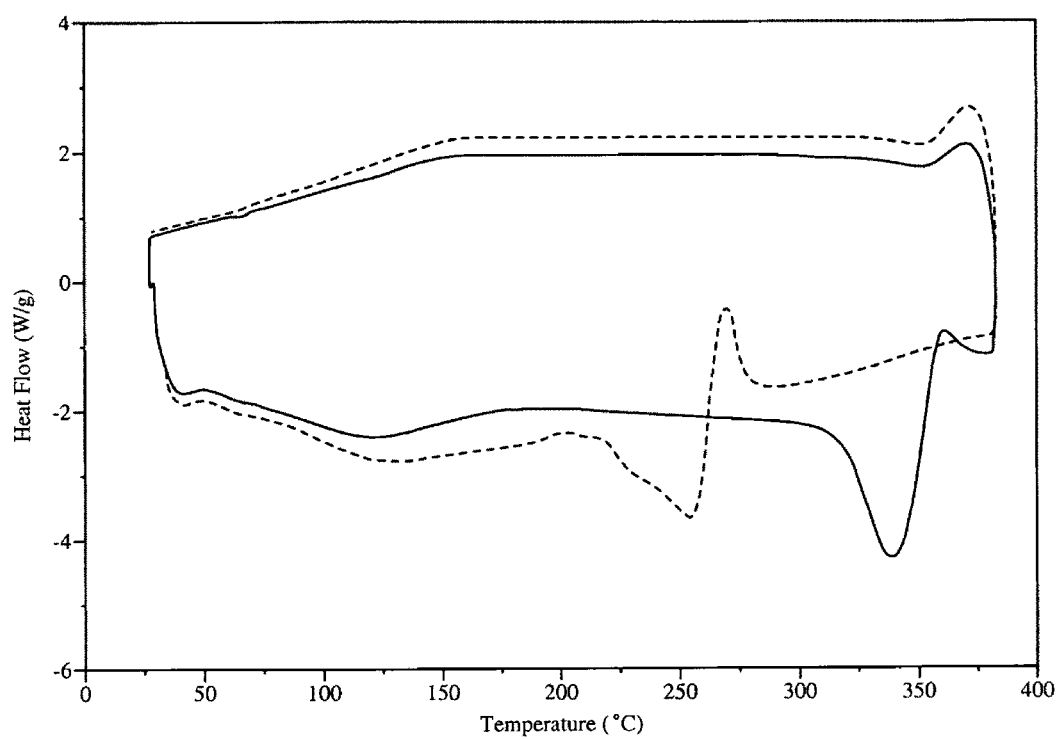
FIG. 5 shows melting point differential scanning calorimeter (DSC) curves for treated [---] and untreated [-----] α-cellulose. The melting point for the treated α-cellulose (NCC) was about 260° C., and the melting point for untreated was about 340° C. The test was done by DSC, Differential Scanning calorimeter, and the instrument was a 2920 MDSC, V2.4F.

FIG. 5 shows differential scanning calorimeter (DSC) curves (melting point) for treated (NCC) and untreated α-cellulose. The melting point for treated α-cellulose (NCC) was about 260° C. The melting point for the untreated α-cellulose was about 340° C. The DSC was a 2920 MDSC, V2.4F.

The bulk density of treated α-cellulose (NCC) was measured as 0.207 g/cm³ in freeze-dried powder form and 0.814 g/cm³ in air-dried and ground powder. Bulk density was measured in a graduated cylinder. The bulk density was determined by mass of the dry sample in the cylinder/bulk volume. The bulk density of α-cellulose was 0.2 g/cm³, the same as freeze-dried treated α-cellulose (NCC).

Treated α-cellulose (NCC/TC) of the current invention is different from "amorphous" cellulose in that the main chemical structure of β-1,4-glucan is retained in the treated cellulose (NCC). The tightly structured multi-layer chains existing in α-cellulose are disrupted and randomly reoriented in treated α-cellulose (NCC).

In summary, a specific example embodiment of the treated cellulose (NCC/TC), specifically, a treated α-cellulose, of the current invention had the following properties:
 a) melting point by differential scanning calorimeter (DSC) of about 260° C.,
 b) bulk density of about 0.2 g/cm³ in freeze-dried powder form,
 c) bulk density of about 0.8 g/cm³ in air-dried and ground powder form,
 d) enzymatic hydrolysis profile using 1 filter paper unit (FPU) cellulase/1 cellobiase unit (CBU) β-glucosidase similar to what is shown in FIGS. 3a)-3g),
 e) FTIR spectrum similar to what is shown in FIG. 4, f water absorption capacity of about 6 to about 8 times its weight in water (highly hygroscopic),
 g) X ray diffraction pattern showing low crystallinity similar to what is shown in FIG. 2, and
 h) morphology without a rigid crystalline structure but rather a sponge-like structure (see SEM FIGS. 1a)-1f)).

The new non-crystalline/low crystallinity cellulose (NCC/TC) can be distinguished from natural α-cellulose by the following properties:
 significantly lower melting point, approximately 260° C.,
 a different bulk density in air-dried and ground powder, about 0.8 g/cm³,
 a FTIR spectrum distinct from natural α-cellulose,
 SEM demonstrates clear differences from natural α-cellulose in morphology, surface area, porosity, and crystallinity,
 an X-ray diffraction pattern distinct from natural α-cellulose and microcrystalline cellulose,
 reactivity about 100 times higher than natural α-cellulose with cellulase, highly hygroscopic in its dry form, absorbing at least about 10 times its own weight in water, forms a highly viscous paste in wet form and when first made, drying converts the paste into various physical forms from fine powder to a rigid solid substance depending upon the method of drying and the moisture content of the paste:

spray-drying or freeze-drying with high moisture content results in a powdery product, freeze-drying under low moisture content results in a loosely structured cake, oven-drying in a container results in a rigid substance, and upon grinding with mortar and pestle, it turns into granules or powder.

As compared to untreated cellulose, a treated cellulose (non-crystalline or low crystallinity cellulose) of the present invention had the following properties:

a) lower melting point, as measured by DSC, than α-cellulose, b) bulk density in the freeze dried powder form similar to that of α-cellulose, c) bulk density in the air-dried and ground powder form higher than that of α-cellulose, d) greater enzymatic hydrolysis using 1 FPU cellulase/1 CBU β-glucosidase than α-cellulose at the same concentration of enzyme, e) FTIR spectrum significantly different than that of α-cellulose, including a lower absorbance near 1429 $cm^{-1}$ and a higher absorbance near 1162 $cm^{-1}$, f) more hygroscopic than α-cellulose, g) water absorption capacity higher than that of α-cellulose, h) X ray diffraction pattern showing a lower major peak and additional minor peaks as compared to α-cellulose or microcrystalline cellulose, i) morphology that is more homogeneous and has higher connectivity relative to α-cellulose morphology, j) higher surface area per unit mass than α-cellulose, k) different porosity than α-cellulose, and l) higher viscosity than α-cellulose when added to water at similar concentrations.

Specifically, a) the melting point is about 80° C. lower than α-cellulose, b) bulk density in the air-dried and ground powder is about 4 times higher than that of α-cellulose, c) about 2 orders of magnitude greater initial enzymatic hydrolysis than α-cellulose at the same concentration of enzyme, d) FTIR spectrum significantly different than that of α-cellulose, including an absorbance about 10-15% lower at 1429 $cm^{-1}$ and an absorbance about 30-60% higher near 1162 $cm^{-1}$, e) water absorption capacity about 5 to about 25 times higher than that of α-cellulose, and f) X ray diffraction pattern having a lower peak at about 2θ=22° and additional minor peaks at higher values of 2θ as compared to α-cellulose or microcrystalline cellulose.

When a treated cellulose material (NCC) of the present invention was ultra-sonicated, it dispersed in water into loose-and-fine structure (from gel to fine dispersant, yet insoluble). It stayed in dispersed form indefinitely and never precipitated.

A treated cellulose (NCC) of the invention can be made, for example, by a process described below in the section Method of Making below and in the Examples.

The invention includes compositions comprising a non-crystalline/low crystallinity cellulose (NCC) of the present invention. For example, a polymer comprising the treated cellulose or a co-polymer comprising the treated cellulose of the invention and at least one other material.

The end product of the process described below has an essentially non-crystalline structure. This results in higher reactivity with other potential reactants. The material can be formed into a homopolymer or copolymer with other monomeric raw materials of plastics (e.g., propylene, styrene, acrylic acid). These polymers can be transformed into fibers, fabrics, foam products, or molded products. This product can also be used as a super absorbent powder because of high hygroscopic property (.about.10 g water/g solid). This product can be used as an ingredient in paper making for production of specialty papers (super absorbing, high tensile strength, etc.).

The treated cellulose and compositions comprising a treated cellulose (NCC) included in the present invention can be used in various applications, e.g., see Applications and Utility.

B. Method of Making

A process to convert refined and/or unrefined cellulosic substances into materials containing non-crystalline cellulose (NCC) of the present invention is described. Refined cellulosic substances include, for example, α-cellulose, microcrystalline cellulose, and refined cotton. Unrefined cellulosic substances include, for example, corn stover, Kraft pulp, hard wood, soft wood, unrefined cotton, and other agricultural residues. Mixtures of various cellulosic substances can also be used as starting material. Other cellulosic starting materials will be apparent to one of ordinary skill in the art. Cellulosic materials are commercially available or otherwise readily available.

In an example embodiment, dry cellulosic materials (i.e., α-cellulose) were ground into granules and/or powders and mixed with strong acid (i.e., concentrated sulfuric acid) under the following example conditions:

| | |
|---|---|
| Concentration of sulfuric acid: | 65 wt %-72 wt % |
| Liquid/solid proportion: | 1 dry gram of solid cellulosic material to 1-4 ml of sulfuric acid of the a bove strength |
| Temperature: | 20-60° C. |

Though it is not necessary to size the cellulosic material, it is preferred that sizing, e.g., grinding, is done prior to mixing with the strong acid. Sizing makes it easier to wet the cellulosic material and mix it with the acid.

The acid used is a strong acid, for example, concentrated sulfuric acid. One of ordinary skill in the art can choose an appropriate strong acid and concentration of acid to use in a method of the invention.

One of ordinary skill in the art can readily determine an appropriate ratio of strong acid and cellulosic material to use in a method of the invention.

The method can be carried out, for example, at room temperature and pressure. Temperature and time of reaction have a compensating effect, i.e., generally higher temperature requires less reaction time, while lower temperature slows the reaction. At 60° C. the reaction is expected to take about 5-60 minutes. Higher temperatures may require only a couple of minutes. At too high of a temperature, the uniformity of the material will be harder to control due to the reaction occurring so quickly during mixing which allows some of the cellulosic material to potentially break down too far. Low temperatures can essentially stop or significantly slow the reaction. One of skill in the art can determine an appropriate combination of time and temperature for a desired end material.

In the example embodiment, the mixture was agitated using a glass rod until a uniformly wet condition (as determined by visual observation) was attained. The resulting mixture was left for 20-120 minutes at room temperature. Water was then added such that the sulfuric acid concentration in the liquid became 2-10 wt %. The resulting slurry was filtered or centrifuged in order to remove the liquid. The slurry mixture was washed with water and filtered or centrifuged again to remove the residual sulfuric acid. Neutralization with a base (sodium hydroxide or other base component) may optionally be applied to make the final product into a neutral substance.

It is desired that the agitation be by a gradual, gentle method or device. It is desirable that the method be such that it aids in being able to use the minimum amount of acid necessary to wet the material and carry out the reaction. The time of reaction depends on the desired end molecular weight of the end product material (NCC). This is balanced versus a desire to have a good yield of the material. For example, the example embodiments the reaction was performed until the mixture of starting material and acid became a uniformly viscous material. The diluent used was water. Though it is believed other diluents can be used, water is believed to be the most practical diluent. The amount of diluent or end concentration of acid is determined based on ending the reaction. An amount of diluent which quenches the reaction is used. Dewatering, washing, and neutralizing are also steps known to one of skill in the art. One of skill in the art can determine appropriate methods, concentrations, choices of materials, and times to use in a method of the present invention with no more than routine experimentation.

The general overall process is simple: solid-liquid mixing under atmospheric pressure at moderate temperatures and separation of solid from liquid.

The yield of the solid product in the process was near quantitative (above 90% in the example embodiment). There is no decomposition of carbohydrate during the process as evidenced by carbohydrate analysis of the starting material versus the end product. There is a small fraction of the starting material that does not behave like the rest of the material; approximately 5-10% of the starting material ends up not reacting like the rest of the material. Carbohydrate analysis by HPLC is usually done before and after treatment to confirm there was no decomposition during the process.

The end product of the process was obtained initially in a highly viscous paste form. Drying of this end product material converted the paste into various physical forms, from fine powder to a rigid solid substance, depending upon the method of drying and the moisture content of the paste. Freeze-drying with high (e.g., about 90%) moisture content resulted in a powdery product. Spray-drying can also be performed on the material. Freeze-drying under low (e.g., about 50%) moisture content resulted in a loosely structured cake. Oven-drying in a container resulted in a rigid substance. Upon grinding with mortar and pestle, the end product turned into granules or powder. A material of the invention is highly hygroscopic both in powder and granular form. One of skill in the art can determine various methods of drying or sizing the material to achieve a desired end product.

One of ordinary skill in the art can determine further processing steps (and ways of achieving these steps), such as drying, which can be done to the non-crystalline or low crystallinity cellulose product (NCC) in order to place it in a desired form for use. Many further processing steps are conventional in the art. Also, one of skill in the art can determine variations on the method. For example, in order to delay or prevent reaction while the agitation is being performed, it is believed that the mixture could be brought to a low temperature, e.g., 0° C., and then brought up to reaction temperature. It is believed this variation can result in a more uniform end material (NCC).

The present invention includes a non-crystalline or low crystallinity cellulose (NCC) produced by a method comprising a) providing cellulosic material,
b) adding an effective acid in an amount effective to at least wet the cellulosic material,
c) mixing the cellulosic material and the acid under conditions effective to form an essentially uniformly wet condition,
d) letting the mixture sit at ambient conditions for a period of time sufficient to form a viscous fluid,
e) adding water or other diluent in an amount sufficient to lower the acid concentration and to form a slurry,
f) dewatering the slurry, and
g) removing any residual acid from the dewatered slurry to form the non-crystalline or low crystallinity cellulose.

The method can further comprise neutralizing the dewatered non-crystalline or low crystallinity cellulose.

The present invention also includes a method for making a non-crystalline or low crystallinity cellulose (NCC) comprising
a) providing cellulosic material,
b) adding an effective acid in an amount effective to at least wet the cellulosic material,
c) mixing the cellulosic material and acid under conditions effective to form an essentially uniformly wet condition,
d) letting the mixture sit at ambient conditions for a period of time sufficient to form a viscous fluid,
e) adding water or other diluent in an amount sufficient to lower the acid concentration and to form a slurry,
f) dewatering the slurry, and
g) removing any residual acid from the dewatered slurry.

The method can further comprise neutralizing the dewatered non-crystalline or low crystallinity cellulose (NCC). The removing any residual acid can be done by, for example, washing and dewatering steps. The neutralization can be done by addition of a base, for example, sodium hydroxide or potassium hydroxide. The method can also further comprise drying the dewatered slurry after removal of residual acid.

The method can comprise further steps for the purposes of producing chemicals or fuels via fermentation or other chemical processes. For example, the NCC can be then hydrolyzed to produce sugars which are then fermented to produce ethanol.

The invention further includes, more specifically, a method for making a non-crystalline or low crystallinity cellulose (NCC) comprising
a) providing essentially dry, sized cellulosic material,
b) adding about 65 wt % to about 72 wt % concentrated sulfuric acid at about 1 to about 4 ml per gram cellulosic material,
c) mixing the cellulosic material and acid at about 20 to about 60° C. and atmospheric pressure to form an essentially uniformly wet material,
d) letting the mixture sit at ambient conditions for about 5 to about 120 minutes,
e) adding water in an amount sufficient to lower the acid concentration to about 2 to about 20 wt % and to form a slurry,
f) dewatering the slurry, and
g) removing any residual acid from the dewatered slurry.

The method can further comprise neutralizing the dewatered non-crystalline cellulose (NCC) using sodium hydroxide or potassium hydroxide.

C. Applications and Utility

A treated cellulose (NCC) (and the method of producing the treated cellulose) of the present invention can be used for production of fuels from biomass. For example, the treated cellulose (NCC) can be further broken down into sugars and the sugars fermented into alcohols, such as ethanol.

A treated cellulose (NCC) of the present invention can be used as a standard reagent for testing enzyme reactivity. For example, see Example 3 for a method of using the treated cellulose (NCC) as such a reagent.

Additional uses of the treated cellulose (NCC) of the present invention include, for example, use as a food or pharmaceutical additive or paper additive, a hydrogel for medical applications, an absorbent material, or a growth medium for bacteria, fungi, molds or other biological entities.

A treated cellulose (NCC) of the present invention can be used for producing homopolymers and copolymers that could be transformed into fibers, fabrics, foam products, or molded products, for example.

The invention also includes materials and compositions made from the treated cellulose (NCC), for example, paper, a fiber, woven or non-woven fabric, foam, molded product, or molded co-product comprising the non-crystalline or low crystallinity cellulose (NCC) and at least one other material.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Treated α-Cellulose

A process was developed wherein the crystalline structure of α-cellulose was modified into an essentially amorphous form resulting in "non-crystalline cellulose (NCC)".

The overall process was quite simple: solid-liquid mixing under atmospheric pressure at moderate temperatures and separation of the solid from the liquid. The yield of the solid product in the process was near quantitative (above 90%). There was no decomposition of carbohydrate during the process as indicated by carbohydrate analysis.

Dry α-cellulose was ground into granules and/or powders and mixed with concentrated sulfuric acid under the following example conditions:

| | |
|---|---|
| Concentration of sulfuric acid: | 65 weight %-72 weight % |
| Liquid/solid proportion: | 1 dry gram of solid to 1-4 ml of sulfuric acid of the above strength |
| Temperature: | 20-60° C. |

The mixture was agitated until a uniformly wet condition was attained. The resulting mixture was left for 5-60 (or 20-120) minutes at room temperature. Water was then added to the mixture such that the sulfuric acid concentration in the liquid became 2-10 weight %. The resulting slurry was filtered or centrifuged. The mixture was washed with water and filtered or centrifuged again to remove the residual sulfuric acid. Neutralization with a base (sodium hydroxide or other base component) was applied to make the final product unto a neutral substance.

Example 2

Characterization of Treated Cellulose

The treated cellulose (NCC) of Example 1 was then characterized.

Carbohydrate analysis was performed using NREL LAP-002 "Determination of Carbohydrate in Biomass by HPLC" (1996). Ash content was performed using NREL LAP-005 "Determination of Ash Content in Biomass" (1994). Moisture levels were determined using standard procedures. Lignin levels was performed using "Determination of Acid Insoluble Lignin" NREL LAP-003 (1995) and LAP-004 "Determination of Acid Soluble Lignin" (1996).

A SEM was used to take pictures of the original α-cellulose and the resulting NCC using standard procedures. The resulting micrographs at ×200, ×1000, and ×3000 are shown in FIG. 1.

The original α-cellulose, microcrystalline cellulose, and the resulting NCC were subjected to X-ray diffraction using standard procedures. The resulting XRD patterns are shown in FIG. 2.

The original α-cellulose and the resulting NCC were subjected to enzymatic hydrolysis at various enzyme loadings using standard procedures. The results are shown in FIG. 3.

The original α-cellulose and the resulting NCC were subjected to FTIR using the KBr transmission technique on a Nicolet Avatar 360 FTIR ESP spectrometer. The number of scans was set to 50 and resolution was 4.0. Apodization was set for Happ-Genzel. The resulting spectra are shown in FIG. 4.

The original α-cellulose and the resulting NCC were subjected to differential scanning calorimetry (determination of melting point) on a 2920 MDSC, V2.4F using standard procedures. The curves are shown in FIG. 5.

The original α-cellulose and the resulting NCC were measured for bulk density. The NCC was measured in freeze-dried powder, air-dried, and ground powder (from using mortar and pestle) forms. The samples were weighed and measured in a graduated cylinder. Bulk density was mass of the dry sample in the cylinder volume.

Example 3

Measurement of Cellulase Activity

Hydrolysis of cellulose by cellulase enzyme is a solid-liquid heterogeneous reaction. As such, the reaction is strongly affected by the physical resistances caused, most notably, by the crystalline structure. Under the influence of the crystallinity, it is difficult to obtain the intrinsic kinetic information.

The current standard method for measuring the specific activity of cellulase is based on use of filter paper as the standard substrate. It involves reaction of the substrate with cellulase enzyme followed by calorimetric measurement of released glucose. This method suffers from the fact that the overall procedure is very time-consuming and that it has low consistency in replicate tests.

The essentially amorphous form "non-crystalline cellulose (NCC)" of the present invention was used. Non-crystalline cellulose (NCC) was prepared from α-cellulose as described above in Example 1. Due to the non-crystalline nature of NCC, the initial rate of enzymatic hydrolysis was enhanced by about two orders of magnitude above that of natural cellulose. Also, cello-oligosaccharides (COS) were prepared using the same method as the NCC as described in Example 1 but allowing the reaction to proceed for much longer reaction times, e.g., 1-4 hours. The acid is precipitated and the soluble oligomers recovered.

A rapid method of cellulase activity measurement was devised using NCC as the standard substrate. This method started with hydrolysis of NCC with a given enzyme loading (FPU). With use of NCC, ten minutes of reaction time was sufficient to produce glucose, cellobiose, and oligomers in quantities large enough to accurately measure the initial reaction rate. In this method, the reaction was stopped at the 10 minute-point and the total soluble sugars (glucose, cellobiose, and oligomers) were measured. Data from repeated experiments confirmed that the enzyme loading (FPU) was directly correlated with the sugar formation. On the basis of the data obtained, an empirical equation was developed correlating the FPU of cellulase (Spezyme® CP) and the percent of hydrolysis of NCC at the 10-minute point.

Method and Materials

Alpha-cellulose (SIGMA, C-8002) was used for preparation of NCC. NCC was prepared using the method of Example 1.

Enzymatic hydrolysis was done by the NREL standard procedure LAP-009 "Enzymatic Saccharification of Lignocellulosic Biomass" (1996): 1% wt/vol glucan, pH 4.8, 50° C., and 150 rpm.

The cellulose used was Spezyme® CP (Genencor, Lot No. 301-00348-25) supplemented with β-glucosidase at the level of 1 CBU per 1 FPU.

The specific activity of Spezyme® CP was 31.2 FPU/mL.

The conditions for acid hydrolysis of COS were 121° C., 20 minutes, 4% $H_2SO_4$.

TABLE 2

Composition of α-cellulose and NCC by weight percentage components.
Composition of α-cellulose and NCC

| Components Identified | Percentage | |
|---|---|---|
| | α-cellulose | NCC |
| Glucan | 76.06% | 87.16% |
| Xylan | 21.27% | 10.47% |
| Arabinan | 0.70% | 0.00% |
| Galactan | 0.00% | 0.00% |
| Mannan | 0.94% | 0.50% |
| Ash | 0.00% | 1.87% |

Figure 6:
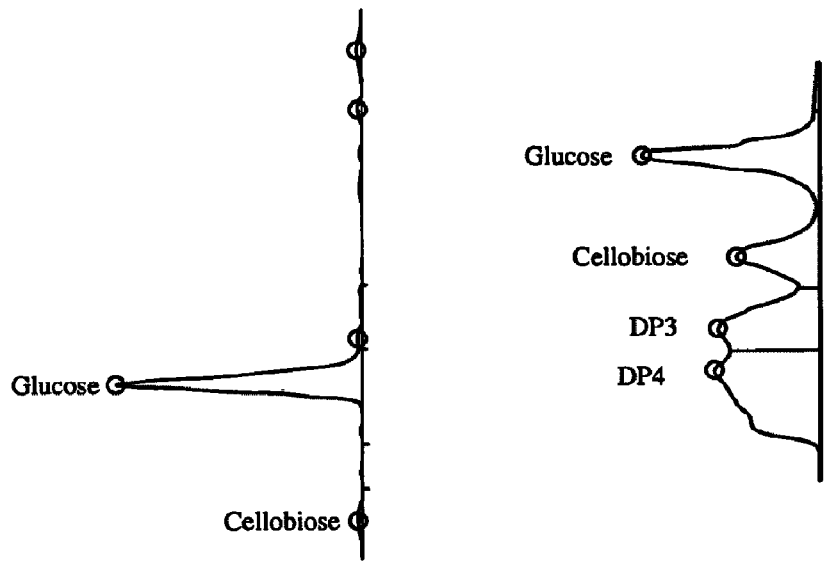
FIG. 6 shows acid and enzymatic hydrolysis of cello-oligosaccharides (COS) for conditions described in Example 3. Acid hydrolysis of COS resulted in 93% glucose yield in 20 min. Enzymatic hydrolysis gave 17.7% glucose yield.
Figure 6:
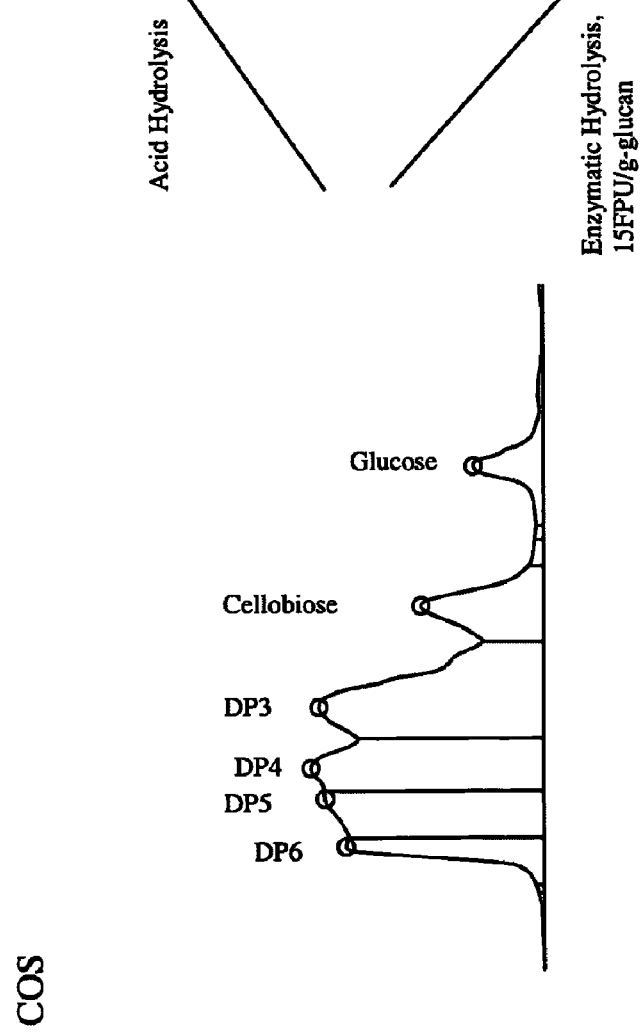

FIG. 6 shows the results of acid and enzymatic hydrolysis of the cello-oligosaccharides (COS). Acid hydrolysis of COS resulted in 93% glucose yield in 20 min. Enzymatic hydrolysis gave 17.7% of glucose yield.

Figure 7:
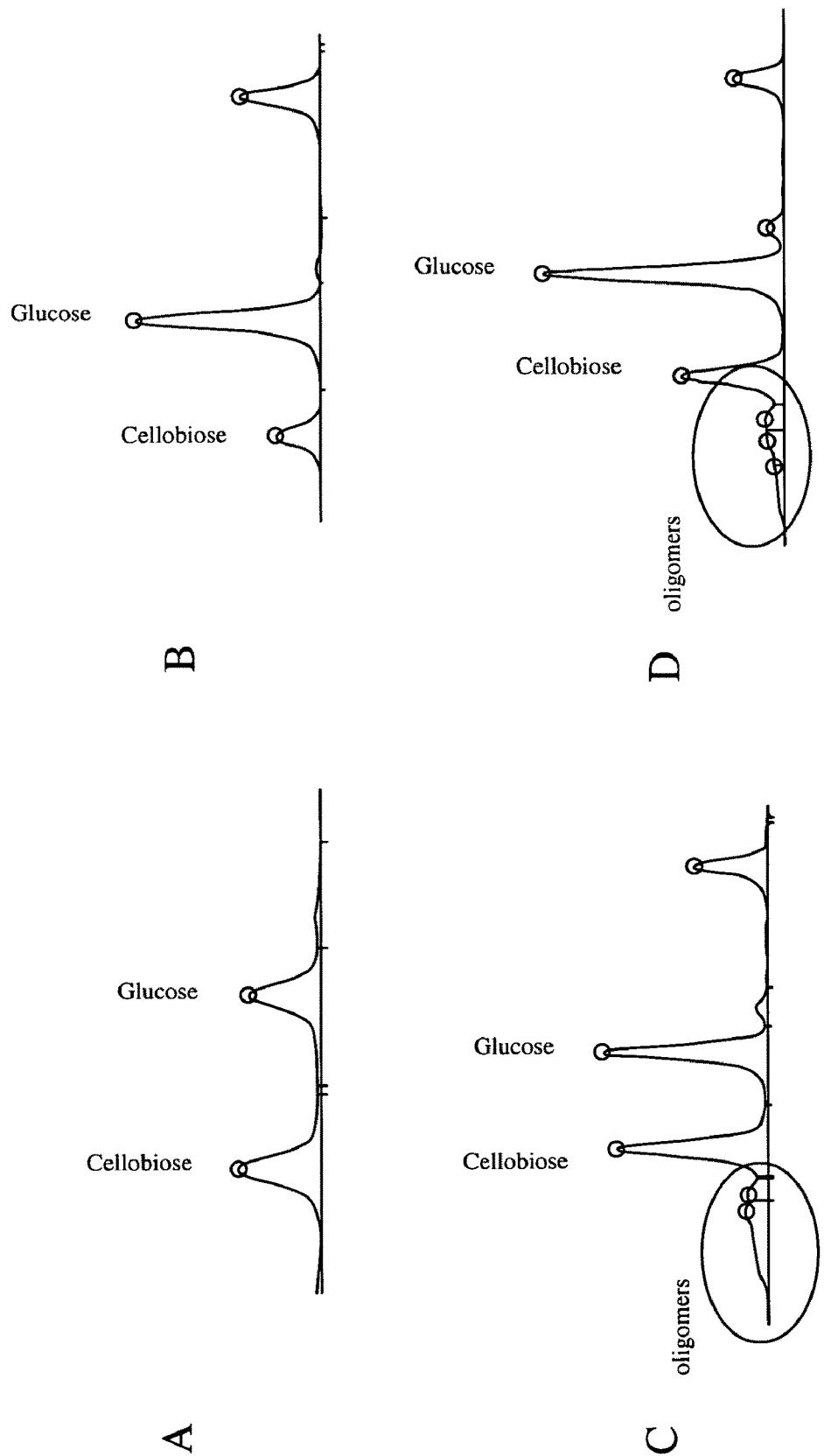
FIG. 7 shows the product distribution from the enzymatic hydrolysis of Avicel® cellulose and NCC for conditions described in Example 3.

FIG. 7 shows the product distribution from the enzymatic hydrolysis of Avicel® cellulose and NCC for conditions described above. FIG. 7A: Avicel® 1 FPU/g glucan (6 hrs.) 7B: Avicel® 1 FPU/g glucan (96 hrs.) 7C: NCC 1 FPU/g glucan (6 hrs.) and 7D: NCC 1 FPU/g glucan (96 hrs.).

Figure 8:
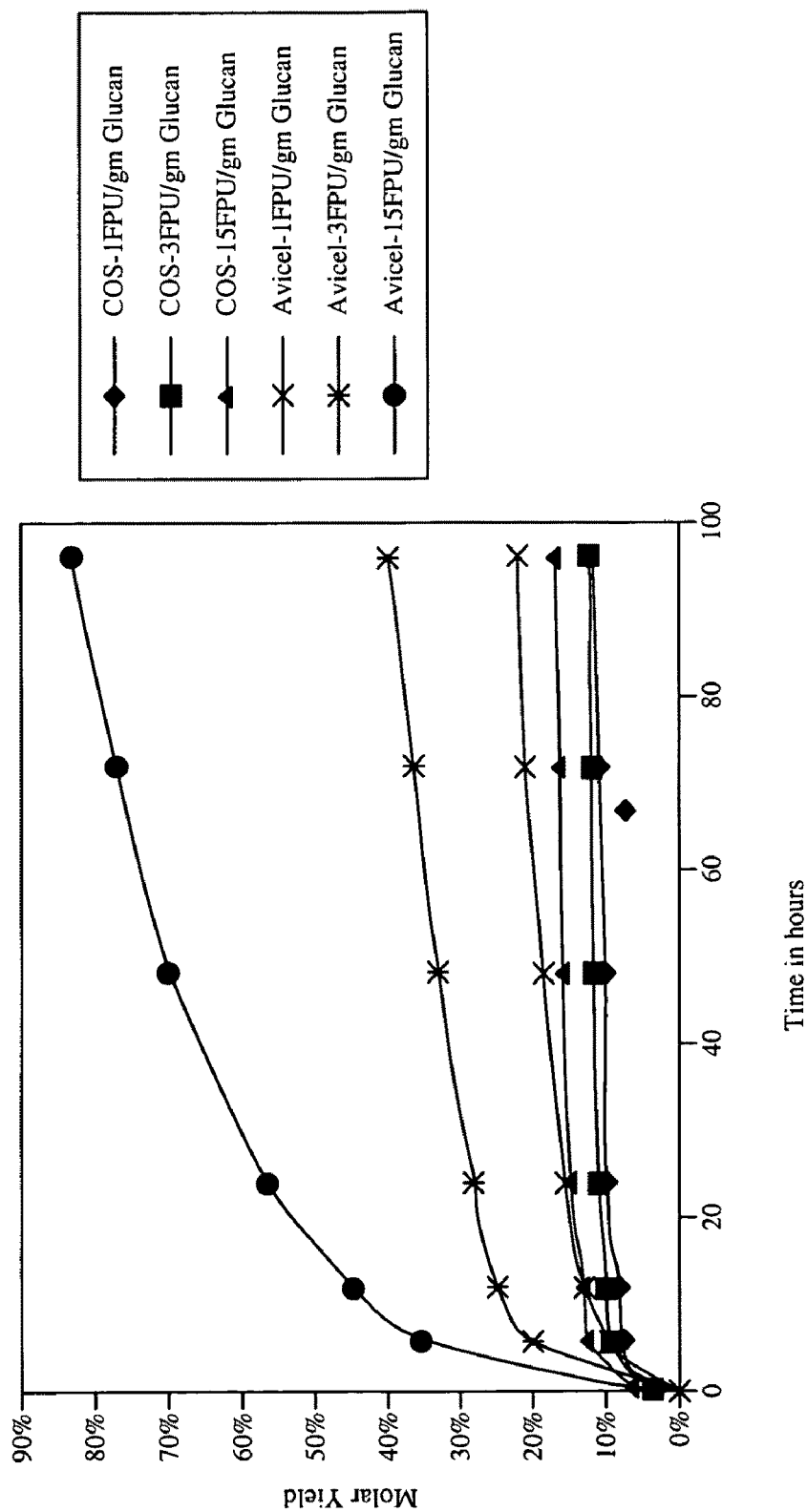
FIG. 8 shows enzymatic hydrolysis of COS and Avicel® for conditions described in Example 3. The lines from top to bottom represent Avicel® with 15 FPU/g glucan (circles), Avicel® with 3 FPU/g glucan (asterisks), Avicel® with 1 FPU/g glucan (X), COS with 15 FPU/g glucan (triangles), COS with 3 FPU/g glucan (squares), and COS with 1 FPU/g glucan (diamonds), respectively. Cello-oligosaccharides are more difficult to hydrolyze than Avicel®.

FIG. 3 demonstrates comparison of the percent hydrolysis for NCC and α-cellulose. FIG. 8 shows the enzymatic hydrolysis of COS and Avicel® for conditions described above. The lines from top to bottom represent Avicel® with 15 FPU/g glucan (circles), Avicel® with 3 FPU/g glucan (stars), Avicel® with 1 FPU/g glucan (X), COS with 15 FPU/g glucan (triangles), COS with 3 FPU/g glucan (squares), and COS with 1 FPU/g glucan (diamonds), respectively. Cello-oligosaccharides were more difficult to hydrolyze than Avicel®.

Figure 9:
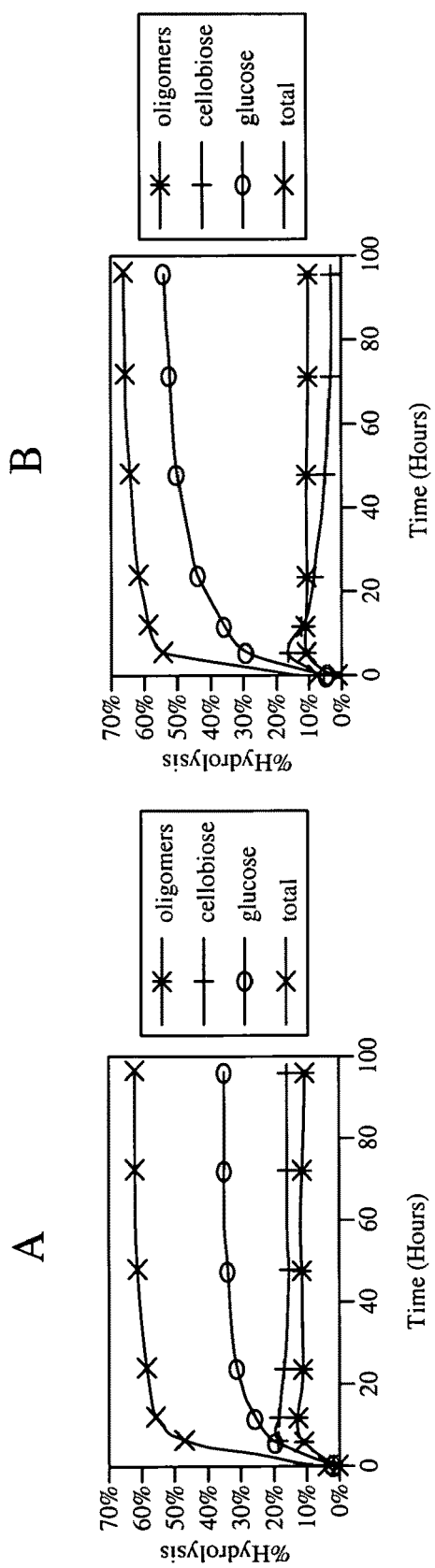
FIG. 9 shows profiles of glucose, cellobiose, and oligomers in hydrolysis of NCC for conditions described in Example 3.

FIG. 9 shows profiles of glucose, cellobiose, and oligomers in hydrolysis of NCC for conditions described above. FIG. 9A: Enzyme loading=1 FPU/g glucan; FIG. 9B: enzyme loading=3 FPU/g glucan. Oligomers were not degraded throughout the reaction.

Figure 10:
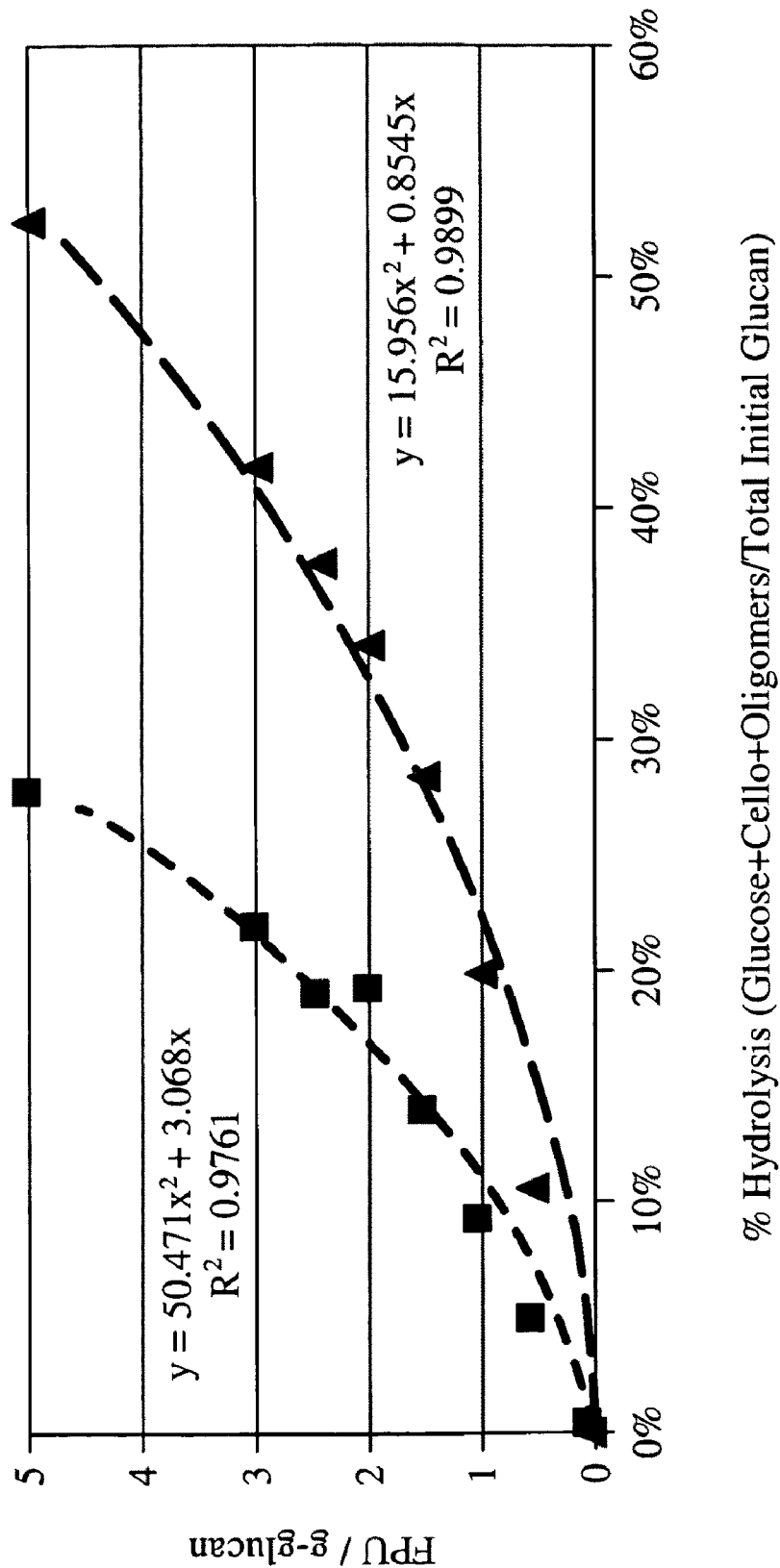
FIG. 10 shows correlation of enzyme loading (FPU/g glucan) with % hydrolysis at 10 minutes. The curve to the right represents the number of FPU as a variable in $2^{nd}$ order polynomial to determine the percentage total formed sugar (glucose+cellobiose+oligomers) based on total initial glucan after 10 minutes enzymatic hydrolysis. The curve to the left represents only glucose plus cellobiose.

FIG. 10 shows a correlation of enzyme loading (FPU/g glucan) with % hydrolysis at 10 minutes. The curve to the right (diamonds) represents the number of FPU as a variable in a $2^{nd}$ order polynomial to determine the percentage total formed sugar (glucose+cellobiose+oligomers) based on total initial glucan after 10 minutes enzymatic hydrolysis. The curve fit gave the equation $y=15.956\ x^2+0.8545\ x$, with $R^2=0.9899$. The curve to the left (squares) represents only glucose plus cellobiose. The curve fit gave the equation $y=50.417\ x^2+3.068\ x$, with $R^2=0.9761$.

Conclusions

Based on the above, the following conclusions were reached:

NCC exhibited a very high initial reaction rate in enzymatic hydrolysis by Spezyme® CP. The reaction essentially ceased after 10 hours.

The hydrolysis products from NCC included glucose, cellobiose and cello-oligosaccharides (oligomers). A significant amount of oligomers were found to accumulate throughout the reaction. It appears that oligomers are inhibitory to cellulose enzyme, especially the endo-glucanase. When cello-oligosaccharides (beta-1, 4 glucan) were produced from α-cellulose and used as the substrate for cellulose and treated separately from the NCC, the oligomers were easily hydrolyzed to glucose by sulfuric acid, but not hydrolyzed significantly using cellulase.

The total soluble sugar content at early reaction time (10 minutes) correlated closely with the nominal activity of enzyme (or amount of enzyme). The same held true if only glucose and cellobiose were counted excluding oligomers.

The close correlation between 10-minute sugar data and FPU indicates that NCC can be used as a standard substrate for rapid measurement of cellulase enzyme activity.

Limitation: This method appears to be most suitable for relative activity measurement at this time because the NCC samples used did not have uniform properties.

Tablet

As described above, NCC has properties very different from natural cellulose. NCC has very low crystallinity, open structure and high porosity. NCC is also hygroscopic. NCC is able to hold water 5-8 times its weight. The cellulose chains in NCC are irregularly arranged. Therefore, higher number of OH groups are exposed than native cellulose. NCC molecules have a high tendency of forming hydrogen-bonds with adjacent molecules which makes NCC an ideal carrier for a medicine tablet.

Tablet Making Tests:

Tablets of ¾ inch diameter were made from NCC and Avicel® PH-104 (a widely used tablet medium) applying 8-30 kilopond (kp) of hardness. The tablets were made without addition of a foreign substance. In both cases, rigid mechanically stable tablets were formed. Physical appearances of the two tablets were indistinguishable.

Water Dissolution Test:

The tablets were dropped into test tubes containing distilled water and were allowed to disperse without agitation. NCC tablets disintegrated faster than Avicel® tablets. The NCC tablets dispersed into very fine uniform gel-like particles due to its highly hygroscopic nature. The Avicel® tablets disintegrated initially into large fragments. Upon agitation and longer storage, the Avicel® tablets eventually dispersed into smaller but uneven-sized particles. After dispersion and agitation, the NCC particles settled down much more slowly than Avicel® particles.

From these observations, NCC has characteristics more suitable as a tablet medium than Avicel® for the following reasons:

NCC has a higher tendency of tablet formation than Avicel®.

NCC tablets disperse faster than Avicel® which is ideal for fast dissolving tablets.

NCC has an open macrostructure thus a higher medicine-holding capacity.

Due to the presence of microspores in NCC, the medicine release pattern is steady and even despite a quick initial release.

The tablet is formed by any method including compression, molding or another method.

Figure 11:
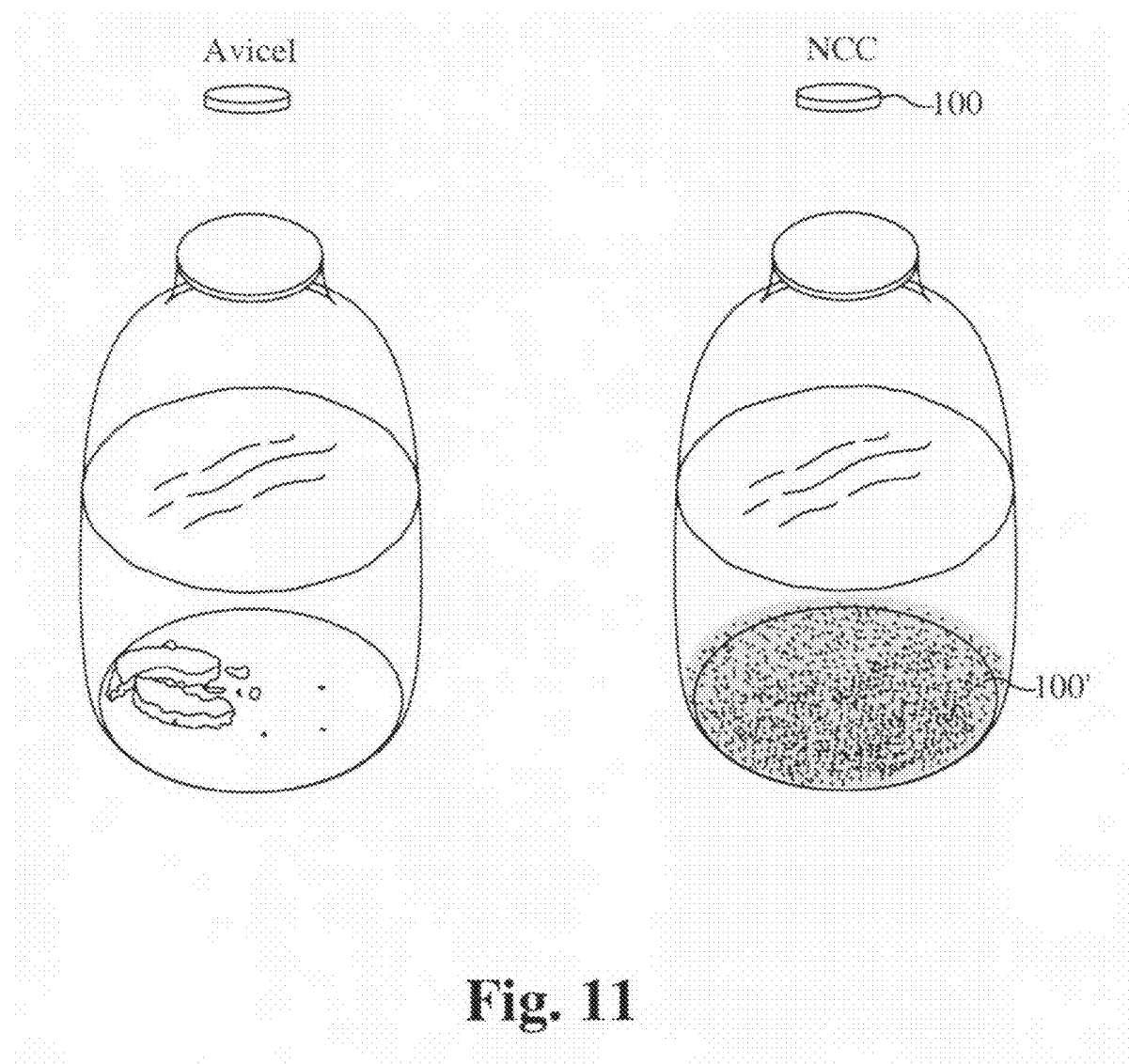
FIG. 11 shows a comparison of NCC and Avicel® tablet dissolution.

FIG. 11 shows a comparison of NCC and Avicel® tablet dissolution. As described above, NCC tablets 100 disperse into very fine, uniform gel-like particles 100' due to its highly hygroscopic nature. In comparison, the Avicel® tablet breaks up into large fragments.

To utilize NCC as a medicine tablet medium, the NCC is formed into a tablet using any method of forming a tablet such as compression and/or via a mold.

In operation, NCC as a medicine tablet medium is able to contain and transport medicine to a desired location in a human body. The tablet then dissolves quickly and uniformly to allow the medicine to properly disperse. Furthermore, due to its open macro structure, NCC is able to hold more medicine than other tablets such as Avicel®.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A tablet comprising a treated cellulose having the following properties:
   a. melting point by differential scanning calorimeter (DSC) of about 260° C.;
   b. bulk density of about 0.2 g/cm3 in freeze-dried powder form;
   c. bulk density of about 0.8 g/cm3 in air-dried and ground powder form;
   d. enzymatic hydrolysis profile using 1 filter paper unit (FPU) cellulase/1 cellobiase unit (CBU) β-glucosidase demonstrating at least about 30% hydrolysis at 15 FPU, at least about 20% hydrolysis at 7 FPU, and at least about 5% hydrolysis at 1 FPU;
   e. water absorption capacity of at least about 6 to about 8 times its weight in water;
   f. morphology without a rigid crystalline structure but rather a sponge-like structure; and
   g. X ray diffraction pattern having a lower peak at $2\theta=22°$ and additional minor peaks at higher values of $2\theta$ as compared to α-cellulose or microcrystalline cellulose.

2. The tablet of claim 1 wherein the treated cellulose is highly hygroscopic.

3. The tablet of claim 1 wherein the tablet consists essentially of the treated cellulose.

4. The tablet of claim 1 further having the property of rapid dispersion in water.

5. The tablet of claim 1 further having the property of an open macro structure.

6. The tablet of claim 1 further having the property of a steady and even medicine release pattern.

7. A tablet comprising a treated cellulose having the following properties:
   a. lower melting point by DSC than α-cellulose;
   b. bulk density in the freeze dried powder form essentially the same as α-cellulose;
   c. bulk density in the air-dried and ground powder form higher than that of α-cellulose;
   d. greater enzymatic hydrolysis using 1 FPU cellulase/1 CBU β-glucosidase than α-cellulose at the same concentration of enzyme;
   e. FTIR spectrum different than that of α-cellulose, including a lower absorbance near 1429 cm$^{-1}$ and a higher absorbance near 1162 cm$^{-1}$;
   f. more hygroscopic than α-cellulose;
   g. water absorption capacity higher than that of α-cellulose;
   h. X ray diffraction pattern having a lower peak at $2\theta=22°$ and additional minor peaks at higher values of 20 as compared to α-cellulose or microcrystalline cellulose;
   i. morphology that is more homogeneous and has higher connectivity relative to α-cellulose morphology;
   j. higher surface area per unit mass than α-cellulose;
   k. different porosity than α-cellulose; and
   l. higher viscosity than α-cellulose when added to water at similar concentrations.

8. The tablet of claim 7 wherein
   a. the melting point is about 80° C. lower than α-cellulose;
   b. bulk density in the air-dried and ground powder is about 4 times higher than that of α-cellulose;
   c. about 2 orders of magnitude greater enzymatic hydrolysis than α-cellulose at the same concentration of enzyme;
   d. FTIR spectrum different than that of α-cellulose, including an absorbance about 10-15% lower at 1429 cm$^{-1}$ and an absorbance about 30-60% higher near 1162 cm$^{-1}$;
   e. water absorption capacity about 5 to about 25 times higher than that of α-cellulose; and
   f. X ray diffraction pattern having a lower peak at $2\theta=22°$ and additional minor peaks at higher values of $2\theta$ as compared to α-cellulose or microcrystalline cellulose.

9. The tablet of claim 7 wherein the tablet consists essentially of the treated cellulose.

10. The tablet of claim 7 further having the property of rapid dispersion in water.

11. The tablet of claim 7 further having the property of an open macro structure.

12. The tablet of claim 7 further having the property of a steady and even medicine release pattern.

13. A method of generating a tablet of a treated cellulose comprising:
   a. providing cellulosic material;
   b. adding an effective acid in an amount effective to at least wet the cellulosic material;
   c. mixing the cellulosic material and acid under conditions effective to form an essentially uniformly wet condition;
   d. letting the mixture sit at ambient conditions for a period of time sufficient to form a viscous fluid;
   e. adding water or other diluent in an amount sufficient to lower the acid concentration to quench a reaction between the cellulosic material and acid and to form a slurry, wherein the slurry comprises predominantly non-precipitated cellulosic material, the acid and the water or other diluent;
   f. dewatering the slurry;
   g. removing any residual acid from the dewatered slurry to form the treated non-crystalline or low crystallinity cellulose; and
   h. forming the cellulose into a tablet.

14. The method of claim 13 wherein forming the cellulose into the tablet is by compression.

15. The method of claim 14 wherein a range of 8-30 kiloponds of hardness is applied when forming the tablet.

16. The method of claim 13 wherein forming the cellulose into the tablet is by using a mold.

17. The method of claim 13 wherein the method of generating the tablet of the treated cellulose consists essentially of step a through step h.

* * * * *